United States Patent
Osborn, III et al.

(10) Patent No.: US 7,713,253 B2
(45) Date of Patent: May 11, 2010

(54) DEFORMABLE TAMPON COMPRISING AN INNER WRAP AND OUTER WRAP

(75) Inventors: Thomas Ward Osborn, III, Clifton, OH (US); Brian Kenneth Burgdorf, Norwood, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 278 days.

(21) Appl. No.: 10/900,821

(22) Filed: Jul. 28, 2004

(65) Prior Publication Data

US 2006/0025740 A1 Feb. 2, 2006

(51) Int. Cl.
*A61F 13/15* (2006.01)
*A61F 13/20* (2006.01)

(52) U.S. Cl. .................. 604/385.18; 604/385.17

(58) Field of Classification Search .......... 604/904, 604/385.17, 385.18; 424/430, 431
See application file for complete search history.

(56) References Cited

U.S. PATENT DOCUMENTS

| | | | |
|---|---|---|---|
| 1,977,133 A * | 10/1934 | Linard | ........................ 604/363 |
| 3,559,646 A | 2/1971 | Mullan | |
| 3,712,305 A | 1/1973 | Wennerblom | |
| 3,812,856 A | 5/1974 | Duncan | |
| 3,815,601 A | 6/1974 | Schaefer | |
| 4,041,947 A | 8/1977 | Flam et al. | |
| 4,041,948 A * | 8/1977 | Flam et al. | ................... 604/369 |
| 4,278,088 A * | 7/1981 | Reeves et al. | ............... 604/368 |
| 4,335,720 A | 6/1982 | Glassman | |
| 4,341,214 A | 7/1982 | Fries | |
| 4,374,522 A | 2/1983 | Olevsky | |
| 4,617,326 A * | 10/1986 | Bjornberg et al. | ........... 428/536 |
| 5,108,383 A | 4/1992 | White | |
| 5,185,010 A * | 2/1993 | Brown, Jr. | ................... 604/379 |
| 5,884,771 A | 3/1999 | McCormick | |
| 6,533,771 B2 | 3/2003 | Suga et al. | |
| 6,635,800 B2 * | 10/2003 | Jackson et al. | .............. 604/378 |
| 2003/0149416 A1 | 8/2003 | Cole et al. | |

FOREIGN PATENT DOCUMENTS

| | | |
|---|---|---|
| FR | 870 986 | 4/1942 |
| GB | 373 848 | 6/1932 |
| WO | WO 02/056811 A2 | 7/2002 |

OTHER PUBLICATIONS

PCT International Search Report dated Mar. 11, 2005.

* cited by examiner

*Primary Examiner*—Melanie J Hand
(74) *Attorney, Agent, or Firm*—James E. Oehlenschlager

(57) ABSTRACT

An improved design for tampons comprising a first material positioned within a flexible inner wrap; the inner wrap is encased by a flexible, fluid permeable outerwrap with a second material positioned between the inner and outer wrap. Either the first or second material may be absorbent or nonabsorbent. The first and second materials can take many physical forms including particles, fibers, agglomerates, powders, gels, foams, beads and mixtures thereof.

15 Claims, 2 Drawing Sheets

DEFORMABLE TAMPON COMPRISING AN INNER WRAP AND OUTER WRAP

FIELD OF THE INVENTION

This invention relates to highly deformable tampons including tampons.

BACKGROUND OF THE INVENTION

Generally catamenial tampons are rigid, have very low resiliency, and are small in their cross sectional dimension in order to provide insertion, wearing, and removal comfort. Generally, self-sustaining tampons are limited with respect to containment, capacity, and absorption rates. Self-sustaining tampons are generally self-sustained into a cylindrical form and do not expand until contacted by fluid. Self-sustaining tampons range in size from about 0.8 cm to 2.0 cm in diameter and from 2 cm to 7 cm in length. The relatively small dimensions of self-sustaining tampons tend not to fill the vaginal cavity entirely, allowing menses to flow around or bypass them. As well, self-sustaining tampons have limited absorption rates and capacity due to their small surface areas and high density. In addition, self-sustaining tampons are considered by many women to be uncomfortable during use.

The tampon of the present invention has a highly deformable configuration. The present invention provides a solution to the drawbacks of the self-sustaining tampons in that its configuration fills the cross-section of the vagina, provides more containment, and has a greater capacity whereby establishing and maintaining a large void volume within the vagina. Comparatively, the tampon has a larger available surface area that provides good absorbency while being comfortable to wear, insert and remove.

BACKGROUND ART

U.S. Pat. No. 3,812,856 issued to Robert Campbell Duncan and Darrel Dayfield Kokx relates to a hydro-dissociative agglomerate tampon and U.S. Pat. No. 3,815,601 relates to a catamenial aggregate absorbent body.

SUMMARY OF THE INVENTION

This invention relates to a tampon to a highly deformable tampon. This is accomplished by a tampon having a first material positioned within a flexible inner wrap. The inner wrap is encased by a flexible, fluid permeable outer wrap and a second material positioned between the inner wrap and outer wrap.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying drawing, in which:

DETAILED DESCRIPTION OF THE INVENTION

Figure 1:
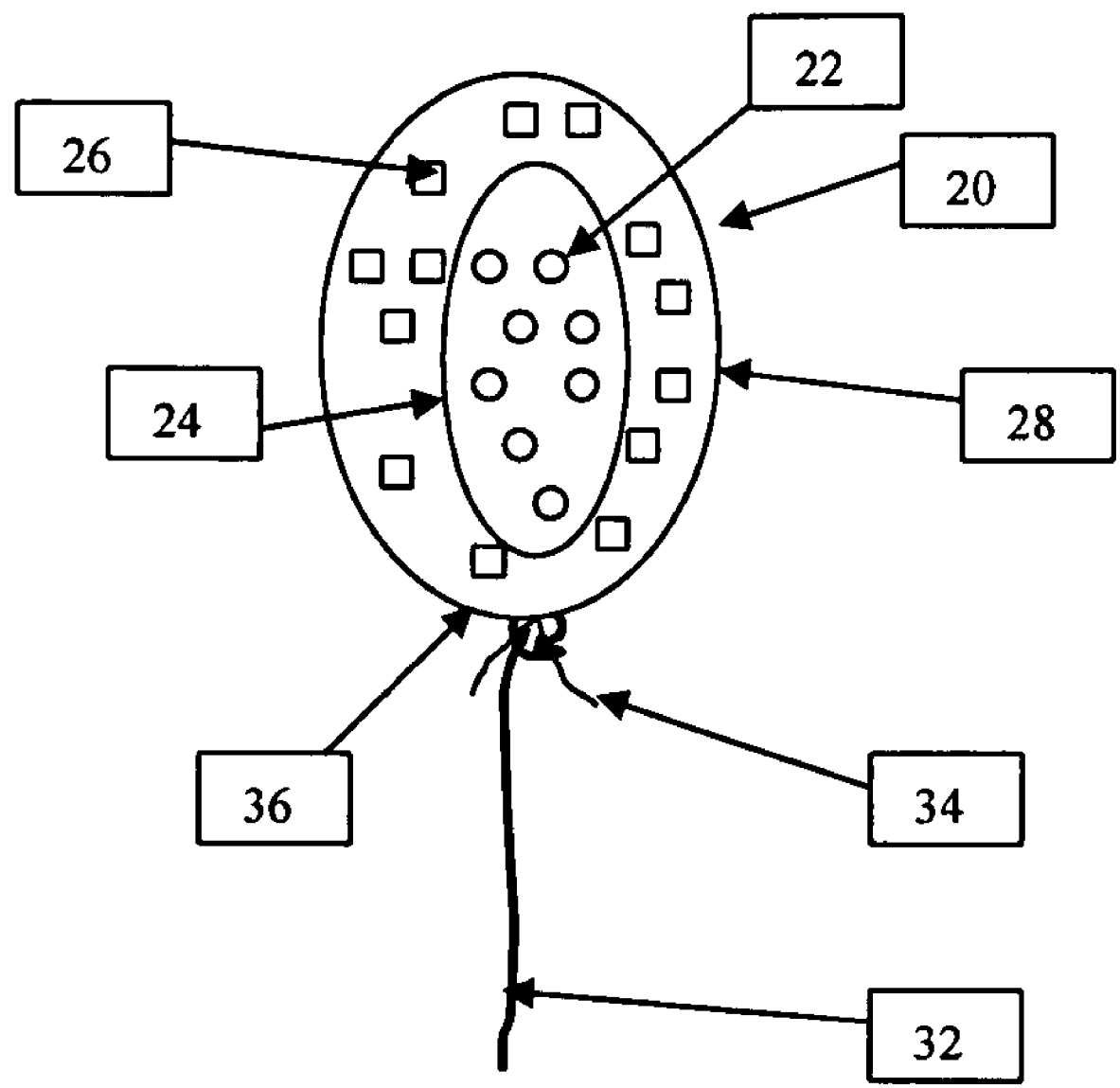
FIG. 1 is a cut away view of the present invention to illustrate the tampon interior.

As used herein the term "absorbency" refers to the amount or quantity of moisture or fluid retained by a material and is measured according to the absorbency test enclosed in the test methods below.

As used herein, the term "beads" refers to a piece or portion of material that can be a variety of geometrical configurations including but not limited to spherical, cylindrical, ovate, or rectangular, trapezoidal, and triangular with rounded edges. In general, the diameters of beads are from about 0.1 mm to about 6.0 mm. The diameters of beads may range in the size from about 1.0 mm to about 4.0 mm.

As used herein, "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

The term "digital tampon," as used herein, refers to a tampon which is intended to be inserted into the vaginal canal with the user's finger and without the aid of an applicator. Thus, digital tampons are typically visible to the consumer prior to use rather than being housed in an applicator.

As used herein, the term "encased" refers to the positioning of an outer element in relation to an inner element whereby the outer element envelops, surrounds, enrobes, or otherwise covers the element material as if in a case.

As used herein "fluid wicking" refers to the ability of a material to carry fluid or moisture by capillary action.

The term "joined" or "attached" as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; i.e., one element is essentially part of the other element.

As used herein "nested" refers to the positioning of an inner element in relation to an outer element in which the inner element fits inside the outer element.

"Retained absorbency is amount of moisture retained by a material measured according to the retained absorbency test enclosed in the test methods below.

As used herein "saturated" refers to the greatest possible amount or quantity of moisture or fluid held or retained by a material. Saturated may also be considered as reaching maximum absorbency at a given pressure, if no pressure is specified then the absorbency would be measured at 0 psi. "Saturation" refers to the condition or state a material reaching maximum absorbency.

As used herein, a tampon has a "self-sustaining shape" when a tampon pledget has been compressed and/or shaped such that it assumes a general shape and size, which is vaginally insertable, absent external forces. It will be understood by one of skill in the art that this self-sustaining shape need not, and preferably does not persist during actual use of the tampon. That is, once the tampon is inserted and begins to acquire fluid, the tampon may begin to expand and may lose its self-sustaining form.

As used herein the term "tampon" refers to any type of absorbent structure that is inserted into the vaginal canal or other body cavities for the absorption of fluid therefrom, to aid in wound healing, or for the delivery of active materials, such as medicaments, or moisture.

As used herein the terms "vaginal cavity," "within the vagina" and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina or hymeneal ring,) and the cervix and is not intended to include the interlabial space, including the floor of vestibule. The externally visible genitalia generally are not included within the term "vaginal cavity" as used herein.

I. Tampon of the Present Invention

FIG. 1 depicts the tampon 20 of the present invention; however, the tampon 20 is not limited to a structure having the particular configuration shown in the FIG. 1. The tampon of the present invention in FIG. 1 comprises an outer wrap 28 encasing an inner wrap 24 that is positioned around a first material 22. The outer wrap 28 is cut away to show the second material 26 that is positioned between the inner wrap 24 and the outer wrap 28. At the center of the cut away view shown is the first material 22, surrounding the first material 22 is the inner wrap 24 and at periphery of the cut away is the outer wrap 28. Between the inner wrap 24 and the outer wrap 28 is the second material 26. Notice that the inner wrap 24 is nested within the outer wrap 28. The first material 22 and second material 26, in FIG. 1, depicts particles of absorbent foam-like material. The outer wrap 28 is secured around the inner wrap 24 by a closure mechanism 30 that is proximate to the withdrawal end 36 of the tampon 20. The skirt portion 34 may extend beyond the closure mechanism 30 at the withdrawal end 36. The withdrawal member 32 is attached to the outer wrap 28. Not to be bound by theory, the Inventors believe the configuration of the present invention may be useful in physically isolating materials and for separating the tampon's acquisition function from the tampon's storage function. The Inventors also believe the present invention may facilitate fluid gradients, and maintain or improve acquisition rates.

a. Inner Wrap and Outer Wrap:

The material that comprises the inner wrap 24 and outer wrap 28. The inner wrap 24 and the outer wrap 28 material in its pre-assembled state may be a two dimensional rectangular, but other shapes such as trapezoidal, triangular, hemispherical, chevron, hourglass shaped, and circular may also be acceptable. Moreover, the inner wrap 24 and outer wrap 28 material in its pre-assembled state may be three dimensional such as cylindrical, cubical, conical, spherical or any other multisided shape. The outer wrap 28 and inner wrap 24 may be rectangular and may measure of from about 1 inch (2.54 cm) to about 5 inches (12.7 cm) in length and from about 1 inch (2.54 cm) to about 5 inches (12.7 cm) in width. As well, the inner wrap 24 is smaller in size than the outer wrap 28 and has a measure of from about 0.5 inch (1.27 cm) to about 4.5 inch (11.4 cm) in length and from about 0.5 inch (1.27 cm) to about 4.5 inch (11.4 cm) in width. Both the inner wrap 24 and outer wrap 28 may preferably be flexible. Both the inner wrap 24 and outer wrap 28 maybe stretchable or elastic. The inner wrap 24 may be attached or detached from the outer wrap. The outer wrap 28 is fluid permeable. The inner wrap 24 may be fluid permeable or fluid impermeable.

The inner wrap 24 and outer wrap 28 material can be comprised of many materials including woven, non-woven materials, folded tissues, films (such as apertured formed thermoplastic films, apertured plastic films, reticulated thermoplastic films, and hydroformed thermoplastic films) or foams (such as porous foams and reticulated foams), that may comprise a blend of natural fibers, synthetic fibers or natural and synthetic fibers. The natural fibers include rayon, cotton, wood pulp, flax, and hemp. Such acceptable types of rayon include GALAXY Rayon (a tri-lobed rayon structure) available as 6140 Rayon from Acordis Fibers Ltd., of Hollywall, England, SARILLE L rayon (a round cross-section fiber rayon), also available from Acordis Fibers Ltd. and SX 275-123 produced by Green Bay Nonwovens, Green Bay, Wis. The synthetic fibers can include but are not limited to fibers such as polyester (such as BIONELLE, biodegradeable polyester) polyolefin, nylon, polypropylene, polyethylene, polyacrylic, vinyl polyacetate, polyacrylate, cellulose acetate or bicomponent fibers.

The fibers may have hydrophobic finishes, hydrophilic finishes, or combinations of hydrophobic or hydrophilic finishes. The fibers may be inherently hydrophilic or hydrophobic, or may be treated to provide such properties. The blend of fibers forming the overwrap can be made by any number of techniques. The blends may be carded on webs. Commonly, carded webs that are hydroentangled, thermally bonded, and resin bonded all have application. In the latter case, all natural fiber may be used with a significant portion of binder (10-30% is common). Spunbond and meltblown processes, combining synthetic fibers extruded/spun onto/into a mat or carded web of natural fibers provide other acceptable techniques. The basis weight of the material may fall into a range from about 10 to about 100 grams per square meter, or typically from about 15 to about 40 grams per square meter.

The inner wrap 24 and outer wrap 28 materials can be comprised of a material known as COROLIND nonwoven material, which is obtainable from BBA NONWOVENS under the tradename PE HPC-2, code T23FOR. A different composition of the first and second materials 22, 26 is 50% rayon, 50% polyester hydroentangled available as BBA 140027. Alternatively, the inner wrap 24 and outer wrap 28 material can be comprised of a material that is dual layered with an outside and inside layer, made in accordance with U.S. Pat. No. 5,273,596. In this case, the outside layer is a 75% hydrophilic polypropylene with a 2.2 denier and 25% 1.5 denier rayon. The inside layer is 25% hydrophilic polypropylene with a 2.2 denier and 75% 1.5 denier rayon. The basis weights of the layers can vary. A typical version has from about 10 to about 15 g/m$^2$ in each layer. The resultant material is 50% rayon 50% polypropylene thermally bonded blend with a basis weight from about 20 to about 30 g/m$^2$. Both materials are produced by BBA Corporation of South Carolina, U.S.A.

The inner wrap 24 and outer wrap 28 can be comprised of a single layer of material, or may also be layers of material. The layers may be two or more layers of the same materials. Alternatively, the layers may be two or more different materials.

If the inner wrap 24 is fluid impermeable, the inner wrap 24 may function to facilitate spreading of the material in the vaginal cavity, provide structure to the tampon as a whole and containment of materials.

The inner wrap 24 and outer wrap 28 may be mechanically altered to achieve low modulus stretch by processes such as, ring rolling, creping, MICREXing, and SELFing as described in U.S. Pat. No. 5,518,801 issued to Chappell on May 21, 1996, incorporated herein by reference.

b. First Material and Second Material:

The first material 22, which is positioned within the inner wrap 24, and second material 26, which is positioned between the inner wrap 24 and the outer wrap 28, can be comprised of the same material or different materials in the various alternatives. The first material 22 and second material 26 can take many physical forms including particles, fibers, agglomerates, powders, gels, foams or beads and mixtures thereof. Sizes of particles range from fine powders to about 8 mm. The dimensions of materials are measured without a confining pressure. The first material 22 and second material 26 may be of any shape known in the art including but not limited to rods, cones, spheres, squares, chevrons, cylindrical, ovate, rectangular, trapezoidal, triangular or amorphous. The first material 22 and second material 26 may be comprised of one material or may include blends of materials. Blends may include different materials, different sized particles, or different shaped particles. The first material 22 and second material 26 may include a blend of the same type of material with different sizes and different shapes. Alternatively, the first material 22 and second material 26 may include a blend of different type of materials of the same size and same shape. The surface charges of the first material 22 and second material 26 may be the same or different. The difference in surface charges may be altered via the addition of charged polymers to the outer surface of the particles or by using cationic absorbents. For example, a quatinized chitosan may be used as the second material 26 and a HIPE foam may be used as the first material 22. The first material 22 and second material 26 may non-absorbent or absorbent.

i. Non-Absorbent Materials:

The first material 22 and second material 26 may be non-absorbent materials such as silica, plastic beads, kratons, polyurethane, rubbers, polyethylene, polypropylene, polyester, and polyesters. Such non-absorbent material can change and impart properties to the tampon structure such as facilitating spread of the tampon within the vaginal cavity and delivery of medicines.

ii. Absorbent Materials:

The first material 22 and second material 26 may include absorbent materials such as but not limited to cotton; rayon; polysaccharides; comminuted wood pulp, which is generally referred to as airfelt; creped cellulose wadding; hydrogel polymer gelling agents; meltblown polymers including coform; chemically stiffened, modified or cross-linked cellulosic fibers; synthetic fibers including crimped polyester fibers, staple fibers; peat moss; absorbent foams absorbent foams (such as those disclosed in U.S. Pat. No. 3,994,298 issued to DesMarais on Nov. 30, 1976, U.S. Pat. No. 5,795,921 issued to Dyer, et. al,) capillary channel fibers (such as those disclosed in U.S. Pat. No. 5,356,405 issued to Thompson, et. al on Oct. 18, 1994), high capacity fibers (such as those disclosed in U.S. Pat. No. 4,044,766 issued Kaczmarzk et al. on Aug. 30, 1977), superabsorbent polymers or absorbent gelling materials (such as those disclosed in U.S. Pat. No. 5,830,543 issued to Miyake, et al on Nov. 3, 1998, U.S. Pat. No. 4,044,766 issued Kaczmarzk et al. Aug. 30, 1977 incorporated by reference herein); superabsorbent polymers or absorbent gelling materials; (such as those disclosed in U.S. Pat. No. 5,830,543 issued to Miyake, et al incorporated by reference herein) absorbent sponges; tissue including tissue wraps and tissue laminates; alginates; excipients (such as sodium starch glycolate sold under the name EXPLOTAB by Penwest Pharmaceuticals, Co., Patterson, N.J.), polymers or co-polymers of maleic anhydride (such as FIBERDRY by Camelot Technologies, Ltd. High River, AB, Canada), chitosans; cationic cellulosic polymers; polysaccarides or any equivalent material or combinations of materials, or mixtures of these.

Any suitable cotton may be used as first material 22 and second material 26. Suitable cotton material includes, long fiber cotton, short fiber cotton, cotton linters, T-fiber cotton, card strips, and comber cotton. Preferably, the cotton should be scoured and bleached cotton absorbent with a glycerin finish, or other suitable finish. The rayon used in the first material 22 and second material 26 may be any suitable type typically used in disposable absorbent articles intended for in vivo use. Such acceptable types of rayon include GALAXY Rayon (a tri-lobed rayon structure) available as 6140 Rayon from Acordis Fibers Ltd., of Hollywall, England. SARILLE L rayon (a round fiber rayon), also available from Acordis Fibers Ltd. is also suitable.

Other absorbent materials may be used for the first material 22 and second material 26 may include for example, carboxymethyl cellulose, primarily insoluble, cross-linked carboxylmethyl cellulose, polyacrylimides, primarily crosslinked, specific starch derivatives, polyacrylates, and polyurethane all of which are well known in the art.

Gel compositions may be used for the absorbent materials 22 such as those disclosed in U.S. Pat. No. 5,830,543 issued to Miyake, et al. Such gel compositions may include polyacrylamide super-absorbent premixed in water or glycerin to gel. The gelling agent may be water, glycerine, polyethylene glycols, or other materials that will gel the primary absorbent. Various compounds can be added to the gelling agent including surfactants, salts of Na, Mg, Ca, etc or antibacterial agents or bacterial static agents, pH control agents or antioxidants including ascorbic acid.

The gel may absorb fluid and maintain an internal structure, so as to prevent the gel from squeezing out of the retaining layers during wear at body pressures and as it absorbs more menses. An example of this type of material is a fibrous absorbent gelling material with a non-gelling core, so that it maintains its fibrous structure while external surface gels. In this context, the elongated structure of the fibrous gel makes it particularly difficult to penetrate through small pores, voids or apertures of the retaining fabric, non-woven or film. It is believed that the longer the gel fiber the lower the probability of penetrating the inner wrap 24 or the outer wrap 28. Such a gel may include Oasis Fibers made by Technical Absorbents, U.K.

The gels may be used with a combination of materials including mixtures of materials including psyllium, alginates, and various fibers. Gels can be combined with fibers. The length of the fibers or the size of the absorbent fiber may be varied. Longer fibers may be used. Typically fibers in the range of 6 mm to 52 mm can be used, although both longer and shorter fibers may be used depending on gel strength and penetration through the inner wrap 24 and outer wrap overwrap 28 when gelled. Gel compositions may be typically combined with hydrophilic fibers such as, rayon, capillary fibers, fibers, polyethylene, polypropylene, polyester and mixtures thereof. It is believed that the fibers can help wick fluid into the gel core, as well as, keep the core open to more rapidly absorb fluid. Generally hydrophilic fibers may be used.

Various absorbent foams can be used as first material 22 and second material 26. The foams used may be relatively thin, collapsed, polymeric foam materials that, upon contact with aqueous body fluids, expand and absorb body fluid. For example the first and second material may comprise an open celled foam of the "High Internal Phase Emulsion"(HIPE) type or may also include "Thin after Drying" (TAD) HIPE absorbent foam. Such foam materials have cells and holes small enough to provide a high capillary absorptive pressure but large enough to prevent or minimize blockage by the insoluble components of blood and blood based liquids such as menses. Such suitable foams are disclosed in U.S. Pat. No. 5,387,207.

Types of absorbent foams that can be used are based on a wide range of polymers are available, including cellulose, cellulose acetate, cellulosic (rayon), styrene, polyolefins, polyvinyl halides, polyesters, polyvinylidene halides, polyurethanes, melamine/formaldehyde, polystyrene, polyacrylate, polyvinyl alcohol/formaldehyde, viscose (dissolved cellulose), or 2-hydroxyethyl methacrylate.

HIPE absorbent foams can be prepared of an aqueous phase and an oil phase. The aqueous phase is prepared consisting of the ratios of materials as described in Table 1. The oil phase is prepared according to the monomer ratios described in Table 1, all of which include an emulsifier for forming the HIPE. The ingredients for the oil phase are purchased through Aldrich Chemical Co., Inc. (Milwaukee, Wis., USA), unless otherwise specified. The emulsifiers are also prepared according to the proportions described in Table 1 as a % by weight of total monomer mass. One particular emulsifier, diglycerol monooleate (DGMO; Grindsted Products; Brabrand, Denmark) comprises approximately 81% diglycerol monooleate, 1% other diglycerol monoesters, 3% polyglycerols, and 15% other polyglycerol esters, imparts a minimum oil phase/aqueous phase interfacial tension value of approximately 2.5 dyne/cm and has a critical aggregation concentration of approximately 2.9 wt %. The monomers plus the emulsifiers make up the oil phase.

To form the HIPE, the oil phase is weighed into a high-density polyethylene cup with vertical sides and a flat bottom. The internal diameter of the cup is 3" and the height of the cup is 4.75" (these dimensions being primarily for convenience). The aqueous phase is placed in a Lab Glass (Vineland, N.J., USA) jacketed addition funnel Model LG-8432-100 and held at a pour temperature of about 65° C. The contents of the plastic cup are stirred using a Caframo RZR50 (Caframo Limited, Wiarton, Ontario, Canada) stirrer with a six-bladed stirrer rotating at about 300 rpm (adjustable by operator as needed). At an addition rate sufficient to add the aqueous phase in a period of about 2 to 5 minutes, the aqueous phase is added to the plastic cup with constant stirring. The cup is moved up and down as needed to stir the HIPE as it forms so as to incorporate all the aqueous phase into the emulsion.

Then, the HIPE is then polymerized and cured. The HIPE in the 3" plastic caps are capped and placed in an oven set at the cure temperature outlined in Table 1 and a cure time of 18 hours to provide polymeric HIPE foam. Some formulations may require substantially less time for curing (e.g. continuous process), but 18 hours provides enough time for all formulations to cure.

Next, the cured HIPE foam is removed from the cup as a cylinder 3" in diameter and about 4" in length. The foam at this point has residual aqueous phase (containing dissolved emulsifiers, electrolyte, initiator residues, and initiator) about 50-60 times (50-60) the weight of polymerized monomers. The foam is sliced on a Hobart Model 1612 meat slicer (Hobart Corp, Troy, Ohio, USA) to give circular pieces about 0.5 mm to about 15 mm in thickness. These pieces are washed in distilled water and compressed to remove the water 3 to 4 times. In some cases they may be washed and compressed further in 2-propanol about 3 to 4 times. The pieces are then dried in an oven at the cure temperature specified in Table 1 for 18 hours. In some cases, the foams collapse upon drying and must be freeze-dried from the water-swollen state to recover fully expanded foams. Various shapes and sizes of foams may be prepared similarly by use of appropriately shaped vessels in which the HIPE is cured and/or appropriate cutting or shaping. The process for preparing the foams of the present invention may also be a one such as that described in U.S. Pat. No. 5,149,720, issued Sep. 22, 1992 to DesMarais et al. or copending U.S. patent application Ser. No. 08/370,694, filed by DesMarais on Jan. 10, 1995, the disclosure of each of which is incorporated by reference.

The foam pieces are then run through an Imperia SP150 (Turin, Italy) pasta maker to chop them into smaller pieces of varying widths and sizes, which are then comprised into the final tampon.

| | Oil Phase | | | | | | | | | | | Aqueous Phase | | Aqueous: Oil ratio | Cure Temp (° C.) |
|---|---|---|---|---|---|---|---|---|---|---|---|---|---|---|---|
| | Monomers | | | | | | | | Emulsifiers | | | | | | |
| Condition | % $DVB_{55}$ | % EHA | % HDDA | % STY | % IOA | % EHMA | % EGDMA | % NPDMA | % DGMO | % PGS | % DTDMAMS | % $CaCl_2$ | % KPS | | |
| A | 15.1 | 59.9 | | 25 | | | | | 6 | | | 10 | 0.05 | 18:1 | 85 |
| B | 25.5 | 57.5 | 12 | 5 | | | | | 6 | | | 4 | 0.05 | 30:1 | 75 |
| C | | 35 | 35 | | 30 | | | | 5 | | | 4 | 0.05 | 25:1 | 65 |
| D | | 40 | | | | 42 | 18 | | 6 | 1 | | 4 | 0.05 | 30:1 | 65 |
| E | | 42 | | | | 40 | 18 | | 6 | 1 | | 4 | 0.05 | 25:1 | 65 |
| F | | 70 | | 10 | | | 20 | | 6 | 1 | | 4 | 0.05 | 25:1 | 65 |
| G | | 45 | | | | 36 | | 19 | 6 | 1 | | 4 | 0.05 | 25:1 | 65 |
| H | | 40 | | | | 41 | 12 | 7 | 6 | 1 | | 4 | 0.05 | 25:1 | 65 |

* $DVB_{55}$ = divinyl benzene of 55% purity obtained from Dow Chemical of Midland, MI plus styrene; EHA = 2-ethylhexyl acrylate; HDDA = 1,6-hexanediol diacrylate; STY = styrene; IOA =; EHMA = 2-ethylhexyl methacrylate; EGDMA = ethylene glycol dimethacrylate; NPDMA =; DGMO = diglycerol monooleate; PGS = polyglycerol succinate, which is formed from an alkyl succinate and glycerol and triglycerol; DTDMAMS = ditallow dimethyl ammonium methyl sulfate; $CaCl_2$ = calcium chloride; KPS = potassium persulfate;

c. Absorbencies of the First and Second Materials

The first material 22 has a first absorbency and second material 26 has second absorbency. The first absorbency and the second absorbency may be the same or different. One can improve the overall acquisition of fluids of the tampon 20 by using materials of various absorbencies within the inner wrap 24 and between the inner wrap 24 and the outer wrap 28. For example, a fluid gradient may be created that acquires fluid from outside the outer wrap 28 into and through the outer wrap 28 into in the inner wrap 24 by the selecting the first material 22 and second material 26 and positioning them within and between the inner wrap 24 and outer wrap 28, respectively. One non-limiting example can be that the first absorbency of the first material 22 positioned within an inner wrap 24 can be such that it has a greater absorbency than the second absorbency of the second material 26 positioned between the inner 24 and outer wrap 28. As well, the first absorbency of the first material positioned within the inner wrap 24 can be equal to the second absorbency of the second material 26 positioned between the inner 24 and outer wrap 28.

Moreover, the first absorbency of the first material 22 positioned within the inner wrap 24 and the second absorbency of the second material 26 positioned between the inner 24 and outer wrap 28 can be different or the same. The second absorbency positioned material positioned between the inner wrap 24 and outer wrap 28 may be greater than the first absorbency of the first material 22 positioned within the inner wrap 24. The first absorbency of the first material 22 positioned within the inner wrap 24 may be greater than the second absorbency of the second material 26 positioned between the inner wrap 24 and outer wrap 28. The first material 22 and second materials 26 may act as a one way reservoir such that when it is loaded to 50% of saturation and is compressed at 0.5 psi (3.45 kPa) the amount of fluid that will squeeze out of the first material 22 within the inner wrap 24 is less than the amount of fluid that will squeeze out of the second material 26 positioned between the inner wrap 24 and the outer wrap 28.

d. Optional Components i. Closure Mechanism:

The closure mechanism 30 of the inner wrap 24 and outer wrap 28 can be any of the known variety including sewing, gluing, tying with a string, heat sealing or ultrasonic bonding. This could include gathering, such as bringing together of the outer wrap 28 at a longitudinal end to form a closure of the outer wrap 28 at that end, such as, a closure which is omni-directionally gathered radially inwardly, as if drawn by a drawstring.

ii. Skirt Portion:

Optionally, the tampon 20 of the present invention may include a skirt portion 34. A skirt portion 34 may be formed when the outer wrap 28 is closed such that at least a portion of the outer wrap 28 extends below the closure mechanism 30 of the structure. Both the tampon 20 and skirt portion 34 of the outer wrap 28 may reside either entirely, substantially or partially within the vaginal cavity of the wearer during use of the tampon 20. This is achieved by the relative closeness of the skirt portion 34 to the withdrawal end 36 of the tampon 20 as well of the relative size compared to the overall size of the tampon 20. Typically, the outer wrap 28 can extend from about 2 mm to about 30 mm, beyond the closure mechanism 30 proximate to the 36 of the tampon 20.

iii. Withdrawal Member

Optionally the tampon 20 of the present invention will comprise a withdrawal member 32. The withdrawal member 32 may be joined to the tampon 20 for removal of the tampon 20 after use. The withdrawal member 32 may be joined to the outerwrap. Any of the withdrawal members 32, currently known in the art may be used as a suitable withdrawal member 32 including ribbons, loops, tabs, or the like. The withdrawal member 32 may be attached in any suitable manner known in the art including sewing, adhesive attachment, or a combination of known bonding methods. The tampon 20 of the present invention may also be provided with one or more than one withdrawal member 32.

iv. Applicator

The tampon 20 of the present invention may be inserted digitally or through the use of an applicator. Any suitable tampon applicator may also be used for insertion of the tampon 20 of the present invention. One example may include typical "tube and plunger" type arrangement and may be plastic, paper, or other suitable material. An additional example may include a "compact" type applicator.

II. Process of Making

While several methods of making the tampon 20 of the present invention would be apparent to one of skill in the art in light of the disclosure herein, following is a description of one method of making a tampon 20 of the present invention.

The process for making a tampon 20 comprises the steps of providing a first material 22. A flexible inner wrap 24 is provided. The first material 22 is positioned within a flexible inner wrap 24. A flexible, fluid permeable outerwrap 28 is provided. The inner wrap 24 is encased by a flexible, fluid permeable outerwrap. A second material 26 is provided. The second material 26 positioned between the inner 24 and outer wrap 28. Optionally, a closure mechanism 30 and withdrawal member 32 is provided.

III. Test Methods

Absorbency Test

The Absorbency test that is performed on the tampon samples is obtained at 0.25 psi by Syngyna Method found in FDA 21 CFR Ch. 1. The Standard Syngyna Test is as follows:

An unlubricated condom, with tensile strength between 17 Mega Pascals and 30 Mega Pascals is attached to the large end of a glass chamber with a rubber band and pushed through the small end of the chamber using a smooth, finished rod. The condom is pulled through until all slack is removed. The tip of the condom is cut off and the remaining end of the condom is stretched over the end of the tube and secured with a rubber band. A preweighed (to the nearest 0.01 gram) tampon is placed within the condom membrane so that the center of gravity of the tampon is at the center of the chamber. An infusion needle (14 gauge) is inserted through the septum created by the condom tip until it contacts the end of the tampon. The outer chamber is filled with water pumped from a temperature-controlled waterbath to maintain the average temperature at 27±1 C. The water returns to the waterbath. Syngyna fluid (10 grams sodium chloride, 0.5 gram Certified Reagent Acid Fushsin, 1,000 milliliters distilled water) is then pumped through the infusion needle at a rate of 50 milliliters per hour. The test shall be terminated when the tampon is saturated and the first drop of fluid exits the apparatus. (The test result shall be discarded if fluid is detected in the folds of the condom before the tampon is saturated). The water is then drained and the tampon is removed and immediately weighed to the nearest 0.01 gram. The absorbency of the tampon is determined by subtracting its dry weight from this value. The condom shall be replaced after 10 tests or at the end of the day during which the condom is used in testing, whichever occurs first.

Retained Absorbency Tests

Figure 2:
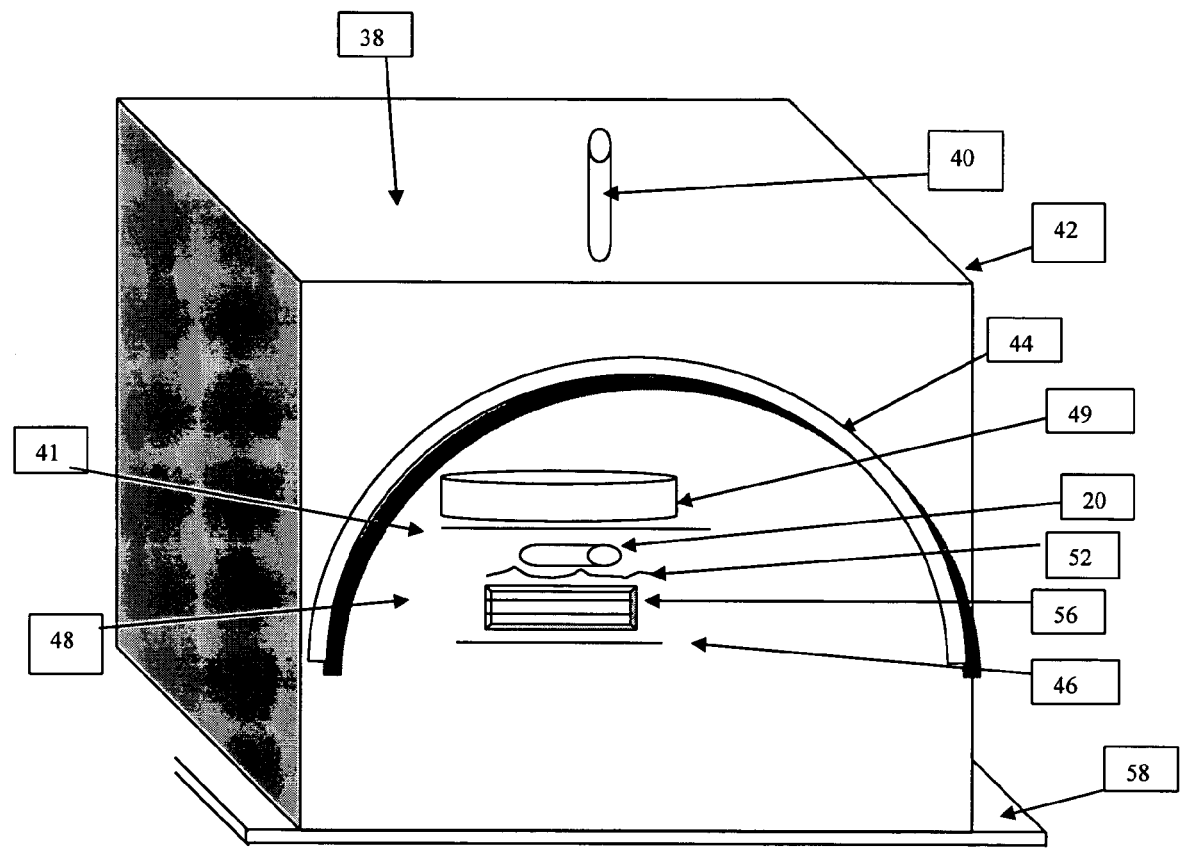
FIG. 2 is a diagram of pneumatic pressure device utilized in the Retained Absorbency Test.

Testing Equipment:

The retained absorbency test utilizes a calibrated balance (Mettler PG802) manufactured by Mettler Instrument Corp., NJ that is accurate to 0.01 g. The retained absorbency test utilizes a pneumatic pressure device, which is shown in FIG. 2. The pneumatic pressure device is comprises a rigid housing 42 with a conformable film 44, a piston 40 and a Magnehelic pressure device (not shown). The piston 40 is connected the rigid housing 42 and a Magnehelic pressure gauge. Custom Tooling Company, Ohio, manufactures the conformable film 44. The Magnehelic pressure gauge is accurate to 0.06 psi manufactured by Dwyer Instruments, Inc, Michigan.

Test Protocol:

First, a layered mass is formed from a layer of film 46 is covered by 15 filter papers 56 that is covered by a sheet of nonwoven 52. The film is SEALWRAP manufactured by Borden packing, MA. The filter papers 56 used #632 that are 5"×5" manufactured by Ahlstrom, Ohio. The nonwoven 52 is 27 g/m$^2$ comprising carded polypropylene manufactured by BBA, Old Hickory, Tenn. under the product code FPN332.

The tampon 20 is placed on top of the film 48, filter paper 56, and nonwoven 52 and a layer of SEALWRAP film 41 is placed on top of the tampon 20 and a layer of polyurethane foam 46 is placed on top of the SEALWRAP 41. The polyurethane foam 46 utilized has a compression modulus of 0.3N/cm2, and a caliper of 12.5 mm at 0 psi, 2.5 mm at 1.0 psi and 2.1 mm at 1.5 psi.

Pressure is applied to the tampon 20 and released and then the weigh of the tampon 20 is taken. Pressure is applied to the tampon 20 at 1.0 psi and held for 6 seconds, and then the pressure is released. The weight of the tampon 20 is taken on the calibrated balance. Next, pressure is applied to the tampon 20 is applied at 1.5 psi and hold for about 6 seconds. The weight of the tampon 20 is taken on a scale. The difference between this weight and the dry weight is designated as retained absorbency at the applied pressure.

IV. Examples

Example 1

A tampon 20 of the present invention is prepared. The tampon 20 comprises two overwraps or bags. The outer bag is made of a nonwoven material called COROLIND that is obtainable from BBA NONWOVENS under the tradename PE HPC-2, code T23FOR with a basis weight of 0.23 g/m$^2$ The material for the outer bag is cut to 3.5 inches by 4 inches, SELFED, folded lengthwise, sewn longitudinally, and closed on one end. The inner bag is made of hydroentagled nonwoven material comprised of 70% rayon and 30% Polyethylene terephthalate obtainable by BBA NONWOVENS under the tradename 140-300 with basis weight of 81 g/m$^2$. The material for inner bag is cut to have the dimensions of about 2.5 inches by 3 inches, SELFED, folded lengthwise, sewn longitudinally, and closed on one end. An absorbent material called excipients in the amount of 0.2 grams is inserted into the inner bag. The inner bag is enclosed and inserted into outer bag. An absorbent foam in the amount of 0.5 gram is inserted between the inner and outer bags. The outer bag is enclosed.

Example 2

A tampon 20 of the present invention is prepared. The tampon 20 comprises three overwraps or bags. The outer bag is made of a material called Sandler Sawabond 4313 with a basis weight of 17 g/m$^2$ cut to 3.5 inches by 4 inches. The material for the outer bag is ring-rolled, folded lengthwise, sewn longitudinally, and closed on one end. The middle bag is made of a material called COROLIND which is a nonwoven that is obtainable from BBA NONWOVENS under the tradename PE HPC-2, code T23FOR with a basis weight of 0.23 g/m$^2$. The material for the middle bag is cut to 3.5 inches by 4 inches, ring-rolled, folded lengthwise, sewn longitudinally, and closed on one end. The inner bag is nonwoven material comprised of 70% rayon and 30% Polyethylene terephthalate obtainable by BBA NONWOVENS under the tradename 140-300 with basis weight of 81 g/m$^2$. The material for the inner bag is cut to dimensions of about 2 inches by 2 inches, ring-rolled, folded lengthwise, sewn longitudinally, and closed on one end. Absorbent gelling fiber in the amount of 0.15 grams is inserted into the inner bag. The inner bag is enclosed and inserted into middle bag. The middle bag is closed and inserted into the outer bag. Compressed cotton chips is the amount of 0.6 grams is inserted between the middle and outer bags. The outer bag is enclosed.

Example 3

A tampon 20 of the present invention is prepared. The tampon 20 comprises two overwraps or bags. The outer bag is an is hydroentangled nonwoven material comprised of 70% rayon and 30% Polyethylene terephthalate obtainable by BBA NONWOVENS under the tradename 140-300 with basis weight of 81 g/m$^2$. The material for the outer bag is cut to 3 inches by 4.5 inches folded lengthwise, sewn longitudinally, and closed on one end. The inner bag is made of a T-bonded Rayon/polypropylene nonwoven, obtainable from BBA NONWOVEMS. The material for the inner bag is cut to the dimensions of about 2 inches by 3 inches. folded lengthwise, sewn longitudinally, and closed on one end. A nonabsorbent material of 0.3 g of 2 mm glass spheres is inserted into the inner bag. The inner bag is enclosed and inserted into outer bag. Absorbent foam in the amount of 0.7 grams is inserted between the inner and outer bags. The outer bag is enclosed.

Example 4

A tampon 20 of the present invention is prepared. The tampon 20 comprises three overwraps or bags. The outer bag is a hydroentangled nonwoven material comprised of 70% rayon and 30% polyethylene terephthalate obtainable by BBA NONWOVENS under the tradename 140-300 with basis weight of 81 g/m$^2$. The material for the outer bag is cut a dimension of 4 inches by 4.5 inches, folded lengthwise, sewn longitudinally, and closed on one end. The middle bag is T-bonded Rayon/Polypropylene nonwoven, which is cut to have the dimensions of about 3 inches by 3 inches, and is folded lengthwise, sewn longitudinally, and closed on one end. The inner bag is made of a nonwoven material obtainable Sandler (Schwarzenbach, Germany) under the tradename Sandler Sawabond 4313 with a basis weight of 17 g/m$^2$. The material for the inner bag is cut to have the dimensions of about 1.5 inches by 1.5 inches, folded lengthwise, sewn longitudinally, and closed on one end. The inner bag is enclosed and inserted into middle bag. An absorbent material of 0.6 g of a 75% cotton and 25% rayon blend of fibers is inserted between the inner and middle bags. The middle bag is closed and inserted into the outer bag. The outer bag is enclosed.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tampon comprising:
a first material having a first absorbency, said first material being encased by a stretchable flexible inner wrap;
said inner wrap being encased by a flexible, fluid permeable outer wrap;
and a second material having a second absorbency being positioned between said inner wrap and said outer wrap;
wherein said inner wrap and said outer wrap are flexible prior to insertion;
wherein the first material and the stretchable flexible inner wrap encasing the first material are spherically shaped.

2. The tampon according to claim 1 wherein said first material is an absorbent material.

3. The tampon according to claim 2 wherein, said absorbent material is selected from the group consisting of cotton; rayon; polysaccharides; comminuted wood pulp; creped cellulose wadding; hydro gel polymer gelling agents; meltblown polymers; carboxy-methyl cellulose; cross-linked carboxylmethyl cellulose; polyacrylimides; polyacrylates crimped polyester fibers; staple fibers; peat moss; absorbent foams; capillary channel fibers; high capacity fibers; superabsorbent polymers; absorbent gelling materials; absorbent sponges; tissue wraps; laminates; alginates; excipients, polymers and co-polymers of maleic acid anhydride; chitosans; cationic cellulosic polymers; polysaccharides and mixtures thereof.

4. The tampon according to claim 1 wherein said second material is an absorbent material.

5. The tampon according to claim 4, said absorbent material is selected from the group consisting of cotton; rayon; polysaccharides; comminuted wood pulp; creped cellulose wadding; hydro gel polymer gelling agents; meltblown polymers; carboxy-methyl cellulose; cross-linked carboxylmethyl cellulose; polyacrylimides; polyacrylates crimped polyester fibers; staple fibers; peat moss; absorbent foams; capillary channel fibers; high capacity fibers; superabsorbent polymers; absorbent gelling materials; absorbent sponges; tissue wraps; laminates; alginates; excipients, chitosans; cationic cellulosic polymers; polysaccharides and mixtures thereof.

6. The tampon according to claim 1 wherein said first absorbency is different from said second absorbency.

7. The tampon according to claim 1 wherein said first absorbency is greater than said second absorbency.

8. The tampon according to claim 1 wherein said tampon comprises a means for closure of said outer wrap.

9. The tampon according to claim 1 wherein said tampon comprises a withdrawal member.

10. The tampon according to claim 1 wherein said inner wrap is fluid permeable.

11. A tampon comprising:
a first plurality of particles, said particles encased by a stretchable flexible inner wrap having a first absorbency;
said inner wrap being encased by a flexible, fluid permeable outer wrap;
and a second plurality of particles being positioned between said inner wrap and said outer wrap having a second absorbency;
wherein said inner wrap and said outer wrap are flexible prior to insertion;
wherein the first plurality of particles and the stretchable flexible inner wrap encasing the first plurality of particles are spherically shaped.

12. The tampon according to claim 11 wherein at least a portion of said first plurality of particles are absorbent particles.

13. The tampon according to claim 11 wherein at least a portion of said second plurality of particles are absorbent particles.

14. The tampon according to claim 11 wherein said first absorbency is different from said second absorbency.

15. The tampon of claim 8 wherein said first absorbency is greater than the second absorbency.

* * * * *

UNITED STATES PATENT AND TRADEMARK OFFICE
CERTIFICATE OF CORRECTION

PATENT NO. : 7,713,253 B2  Page 1 of 1
APPLICATION NO. : 10/900821
DATED : May 11, 2010
INVENTOR(S) : Thomas Ward Osborn, III et al.

It is certified that error appears in the above-identified patent and that said Letters Patent is hereby corrected as shown below:

On the Title Page Item (56)

References Cited, U.S. Patent Documents, delete "4,041,947 A  8/1977  Flam et al.".

Column 12

Line 29, delete "NONWOVEMS" and insert -- NONWOVENS --.

Signed and Sealed this

Seventeenth Day of August, 2010

David J. Kappos
*Director of the United States Patent and Trademark Office*